United States Patent

Hasegawa et al.

Patent Number: 5,498,604
Date of Patent: Mar. 12, 1996

[54] LEWIS-TYPE SUGAR CHAIN DERIVATIVE

[75] Inventors: Akira Hasegawa, 1735-160 Okurayama, Kano, Gifu-shi, Gifu 500; Makoto Kiso, Gifu; Yoshiaki Yoshikuni, Kyoto, all of Japan

[73] Assignees: Nippon Shinyaku Company, Limited; Akira Hasegawa, both of Japan

[21] Appl. No.: 256,991

[22] PCT Filed: Jan. 29, 1993

[86] PCT No.: PCT/JP93/00106
§ 371 Date: Nov. 17, 1994
§ 102(e) Date: Nov. 17, 1994

[87] PCT Pub. No.: WO93/15098
PCT Pub. Date: Aug. 5, 1993

[30] Foreign Application Priority Data

Jan. 31, 1992 [JP] Japan .................. 4-046081
Mar. 18, 1992 [JP] Japan .................. 4-093431
Sep. 16, 1992 [JP] Japan .................. 4-273615

[51] Int. Cl.[6] ............................................. A61K 31/70
[52] U.S. Cl. ......................... 514/27; 514/54; 514/61; 514/62; 536/17.3; 536/17.4; 536/18.7; 536/53; 536/55; 546/184; 546/192; 546/207
[58] Field of Search ......................... 536/18.7, 53, 55, 536/17.3, 17.4; 514/54, 61, 62, 27; 546/184, 192, 207

[56] References Cited

U.S. PATENT DOCUMENTS 4,338,433  7/1982  Matsumura et al. ............. 536/46
4,806,633  2/1989  Ezure et al. ..................... 536/18.5
4,859,767  8/1989  Sugiyama et al. ............... 536/17.4

OTHER PUBLICATIONS

Furui et al. Carbohydr. Res. 1992, 229, C1–C4.
Dumas et al. Bioorg. Med. Chem. Lett. 1991, 1(8), 425–428.
Ichikawa et al. J. Am. Chem. Soc. 1992, 114, 9283–9298.
Kiso et al. J. Carbohydr. Chem. 1993, 12(4–5), 673–7.

Primary Examiner—Douglas W. Robinson
Assistant Examiner—Kathleen Kahler Fonda
Attorney, Agent, or Firm—Rosenman & Colin

[57] ABSTRACT

The object of the present invention is to provide a new SLe-type sugar chain derivative represented by the following formula (I), which is useful as a pharmaceutical and which contains moranoline:

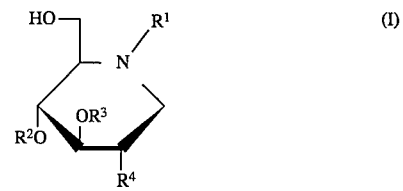

wherein $R_1$ represents hydrogen, a lower alkyl, a lower alkenyl or a lower alkynyl; $R^2$ and $R^3$ differ from each other and represent a galactosyl, sialylgalactosyl or fucosyl group; $R_4$ represents a hydroxyl group or an acetamido group. The present invention comprises a sugar chain derivative containing a moranoline, and having a new structure. Possessing cell adhesion inhibitory activity, the compounds of the present invention antagonizes selectin, serving well in the treatment of inflammation, inflammation-associated thrombosis, asthma and rheumatism, and in the prevention and treatment of immunological diseases and cancer.

10 Claims, No Drawings

LEWIS-TYPE SUGAR CHAIN DERIVATIVE

TECHNICAL FIELD

The present invention relates to a new sialyl Lewis X (hereinafter abbreviated SLe$^x$) type and sialyl Lewis A (hereinafter abbreviated SLe$^a$) type ganglioside sugar chain derivatives represented by the following formula (I), which are useful in pharmaceutical fields such as treatment and prevention of inflammation, intimation-associated thrombosis, asthma, rheumatism, immunological diseases and cancer:

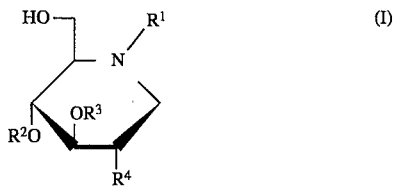

wherein R$^1$ represents hydrogen, a lower alkyl, a lower alkenyl or a lower alkynyl; R$^2$ and R$^3$ independently represent galactosyl, sialylgalactosyl or fucosyl; R$^4$ represents a hydroxyl or acetamido.

BACKGROUND ART

Recent studies have demonstrated that the sugar chains of glycolipids and glycoproteins function as receptors of hormones, bacterial toxins, viruses and others and are profoundly involved in basic dynamic biological phenomena such as cell recognition, differentiation/proliferation, adhesion, transformation, immunity and aging.

Cell surface sugar chains, closely associated with blood group substances such as those of the ABO (H antigen), Lewis (Le antigen) and Ii blood types, are also detected as cancer-related sugar chain antigens. For this reason, there have been studies to apply monoclonal antibodies, that specifically recognize this series of sugar chains, to cancer diagnosis and treatment.

The sialyl Le type sugar chain antigen, a tetrasaccharide sugar chain antigen basically composed of α(2→3) sialyl and α(1→3 and 1→4) fucosylated lactosamine, and found in sialoglycoprotein sugar chains as well as in gangliosides, has been used in serologic diagnosis of cancer as a sugar chain antigen for pulmonary adenocarcinoma and digestive tract cancer. Also, sialyl Le$^x$ sugar chains have very recently been reported as functioning as sugar chain ligands for the leukocyte adhesion factor appearing on vascular endothelial cells during intimation [Lowe, J. B., et al., Cell, 63, 475–484 (1990)].

It is very difficult, however, to obtain these sugar chains as a pure single compound from the living body because they are present in the cell surface layer only in trace amounts.

Against this background various synthetic compounds, including derivatives, have been studied, but none have been known to have moranoline (1-deoxynojirimycin) as a sugar chain component like the compounds of the present invention.

The object of the present invention is to provide a sugar chain derivative that is useful as a pharmaceutical and has a new structure.

DISCLOSURE OF INVENTION

Through extensive research, the present inventors found that the object of the present invention can be accomplished by four types of compounds represented by general formula (I): i. SLe$^x$-type sugar chain derivatives, ii. Le$^x$-type sugar chain derivatives, iii. SLe$^a$-type sugar chain derivatives, which are isomers of the derivatives of terms i. and ii. and have a very similar three-dimensional structure, and iv. Le$^a$-type sugar chain derivatives. The inventors made further investigations based on this finding, and developed the present invention.

The essence of the present invention exists in the structure of the compounds of represented by general formula (I). The compounds of the invention are new compounds not described in literatures, and possess excellent pharmacologic action as stated later.

The lower alkyl for R$^1$ in the formula (I), is preferably a linear or branched alkyl having 1 to 7 carbon atoms, such as methyl, ethyl, n-propyl, isopropyl, n-butyl, isobutyl, t-butyl, n-pentyl, isopentyl, n-hexyl, isohexyl, n-heptyl or isoheptyl.

The lower alkenyl for R$^1$ is preferably a linear or branched alkenyl having 1 to 7 carbon atoms, such as vinyl, propenyl, butenyl, pentenyl, hexenyl or heptenyl.

The lower alkynyl for R$^1$ is preferably a linear or branched alkynyl having 1 to 7 carbon atoms, such as ethynyl, propynyl, butynyl, pentynyl, hexynyl or heptynyl.

The compounds of the present invention are exemplified by the following compounds as well as the compounds described in the Examples of preparation. Those exemplified compounds, however, only show a part of the present invention. Accordingly, the compounds of the present invention are not limited to those exemplified compounds.

O-(5-acetamido-3,5-dideoxy-D-glycero-α-D-galacto-2-nonulopyranosylomc acid)-( 2→3)-O-(β-D-galactopyranosyl)-(1→4)-O-(α-L-fucopyranosyl)-(1→3)]-N-meth- 1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→4)-O-[(α-L-fucopyranosyl)-(1→3)]-N-methyl-1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→4)-O-[(α-L-fucopyranosyl)-(1→3)]-N-methyl-1,5-dideoxy-1,5-imino-D-glucitol O-(5-acetamido-3,5-dideoxy-D-glycero-α-D-galacto-2-nonulopyranosylomc acid)-( 2→3)-O-(β-D-galactopyranosyl)-(1→4)-O-[(α-L-fucopyranosyl)-(1→3)]-N-vinyl- 1,5-dideoxy-1,5-imino-D-glucitol O-(5-acetamido-3,5-dideoxy-D-glycero-α-D-galacto-2-nonulopyranosylomc acid)-( 2→3)-O-(β-D-galactopyranosyl)-(1→4)-O-[(α-L-fucopyranosyl)-(1→3)]-N-allyl- 1,5-dideoxy-1,5-imino-D-glucitol O-(5-acetamido-3,5-dideoxy-D-glycero-α-D-galacto-2-nonulopyranosylomc acid)-( 2→3)-O-(β-D-galactopyranosyl)-(1→4)-O-[(α-L-fucopyranosyl)-(1→3)]-2-acetamido-1,2,5-trideoxy-N-propyl-1,5-imino-D-glucitol O-(5-acetamido-3,5-dideoxy-D-glycero-α-D-galacto-2-nonulopyranosylomc acid)-( 2→3)-O-(β-D-galactopyranosyl)-(1→4)-O-[(α-L-fucopyranosyl)-(1→3)]-2-acetamido-1,2,5-trideoxy-N-pentyl-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→4)-O-[(α-L-fucopyranosyl)-(1→3)]- 2-acetamido-1,2,5-trideoxy-N-heptyl-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-N-methyl-1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-N-propyl- 1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-N-pentyl-1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-N-vinyl- 1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-N-allyl- 1,5-dideoxy-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-2-acetamido-1,2,5-trideoxy-N-propyl-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-2-acetamido-1,2,5-trideoxy-N-pentyl-1,5-imino-D-glucitol O-(5-acetamido-3,5-dideoxy-D-glycero-α-D-galacto-2-nonulopyranosylonic acid)-( 2→3)-O-(β-D-galactopyranosyl)-(1→3)-O-[(α-L-fucopyranosyl)-(1→4)]-2-acetamido-1,2,5-trideoxy-N-heptyl-1,5-imino-D-glucitol The compounds of the present invention possess cell adhesion inhibitory activity, as described in detail in Test Examples later.

Cell adhesion occurs as follows: for example, when leukocytes permeate through an inflammatory area, they adhere to vascular endothelium through capillary blood flow (first adhesion) and roll on the endothelial surface. Next, the leukocytes strongly adhere to the endothelial surface (second adhesion), then migrate into the inflammatory tissue through endothelia intercellular spaces. Thus, cell adhesion occurs in two stages until leukocytes migrate into inflammatory tissue.

As such, cell adhesion is known to be mediated by a group of proteins called as selectin, present in endothelial cells, and its ligand, or a sugar chain of a ganglioside having an Le-type sugar chain antigen or a sialyl Le-type sugar chain antigen, present on the leukocyte surface.

Also, the sialyl Le-type sugar chain antigen, which has a sialyl group, is 30 times as potent as the Le-type sugar chain antigen, which has no sialyl group, in adhesion activity [Proc. Natl. Acad. Sci. USA, 88 (1991)].

Selectin appears on endothelial cells upon endothelial cell stimulation with interleukin 1 or TNF and adheres to leukocytes, but there are some types of selectin which are thought to form thrombi upon the appeearence.

On the other hand, the sialyl Le-type or Le-type sugar chain antigen is thought to be associated with cancer metastasis, since it also exists in metastatic cancer cells. The sialyl Le$^a$ sugar chain antigen, in particular, appears on the surface of almost all types of cancer cells, mainly digestive tract cancer and is thought to play a key role in vascular invasion and metastasis of cancer cells.

Any substance having cell adhesion inhibitory activities inhibits endothelin cell from adhering on leukocytes and cancer cells, and is hence useful in treating and preventing inflammation, inflammation-associated thrombosis, rheumatism, asthma, infectious diseases, immunological diseases, AIDS and cancer.

The compounds of the present invention are therefore useful as an anti-inflammatory agent, antithrombotic therapeutic agent, antiasthmatic/rheumatic therapeutic agent, anti-infectious therapeutic agent, anti-ADS therapeutic agent, and therapeutic and prophylactic agent for immunological diseases and cancer.

The Le$^x$ derivative represented by formula (I) mentioned above can, for example, be prepared as follows:

After the N-tert-butoxycarbonyl derivative of 1-deoxynojirimycin represented by the following formula (wherein Ac and Boc represent an acetyl group and a tertbutoxycarbonyl group, respectively; the same applies below)

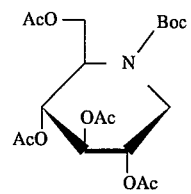

is converted into the following N-benzyloxycarbonyl derivative (wherein Z represents a benzyloxycarbonyl group; the same applies below)

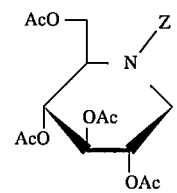

the 4- and 6-hydroxyl groups are protected with a benzylidene group to derive a compound of the following formula (wherein Ph represents a phenyl group; the same applies below):

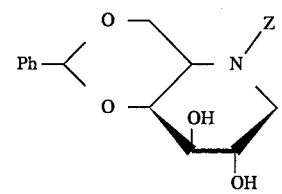

This reaction is followed by position-selective chloroacetylation and subsequent acetylation of the 2-hydroxyl group and dechloroacetylation, to yield an acetyl derivative represented by the following formula:

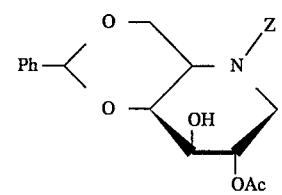

This acetyl derivative is condensed in an inert solvent with the following compound, methyl-2,3,4-tri-O-benzyl-1-thio-β-L-fucopyranoside

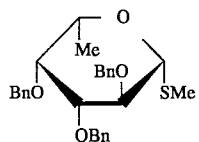

(hereinafter referred to as compound A) (wherein Bn and Me represent a benzyl group and a methyl group, respectively; the same applies below), previously synthesized from L-fucose via several steps, to yield an α-(1→3)-glycoside represented by the following formula at high yield:

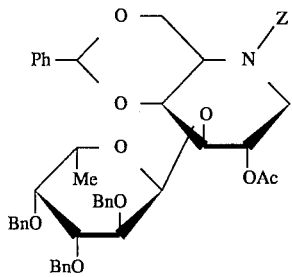

This reaction is carded out in an aprofic solvent in the presence of dimethyl(methylthio)sulfonium triflate (DMTST) or N-iodosuccinimide (NIS) within the temperature range of 0° C.–50° C. for about 1 to 4 hours. The condensation reaction may be preceded by dehydration using a desiccant such as Molecular Sieves if necessary.

Subsequently, the benzylidene group is reductively split off to yield a compound represented by the following formula. This reaction is carried out within the temperature range of 0° C.–50° C. for about 30 minutes to 2 hours:

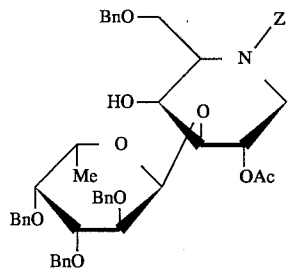

Condensation of the above compound with methyl-2,3,4,6-tetra-O-benzoyl-1-thio-β-D-galactopyranoside (wherein Bz represents a benzoyl group; the same applies below)

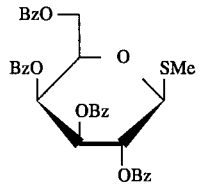

in an inert solvent results in formation of the corresponding trisaccharide derivative:

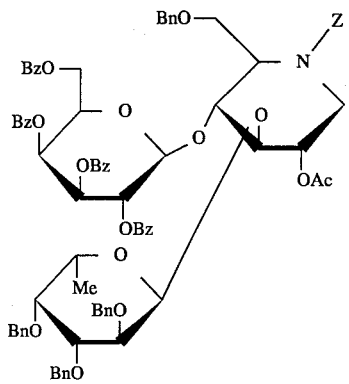

This reaction is carded out within the temperature range of 0° C.–50° C. for about one to several hours. The above-mentioned basic or acidic catalysts can be used as condensing agents; it is preferable that the condensation reaction be carded out in the presence of N-iodosuccinimide (NIS) and trifluoromethanesulfonic acid. The condensation reaction may be preceded by dehydration using a desiccant as necessary. Next, the benzyl group and the benzyloxycarbonyl group are removed by catalytic hydrogenation to yield the following compound,

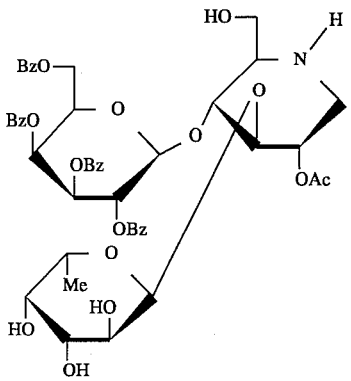

which is then reacted with an alkoxide in an alcohol solvent to remove all O-acyl (acetyl and benzoyl) groups, to synthesize an Le$^x$ sugar chain represented by the following formula, that contains 1-deoxynojirimycin. This reaction is carried out within the temperature range of 0° C.–50° C. for 1 to 2 days.

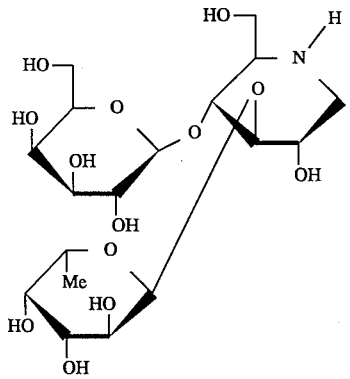

On the other hand, the following compound

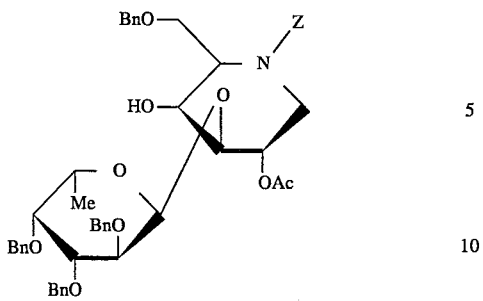

is condensed with the methylthioglycoside derivative of sialyl-α-(2→3)-galactose represented by the following formula (hereinafter referred to as compound B)

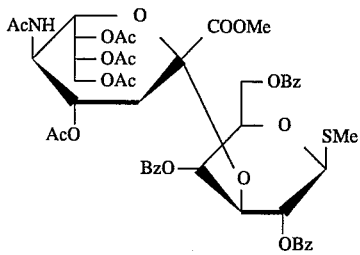

in an inert solvent in the presence of a condensing agent to yield the corresponding tetrasaccharide sugar chain:

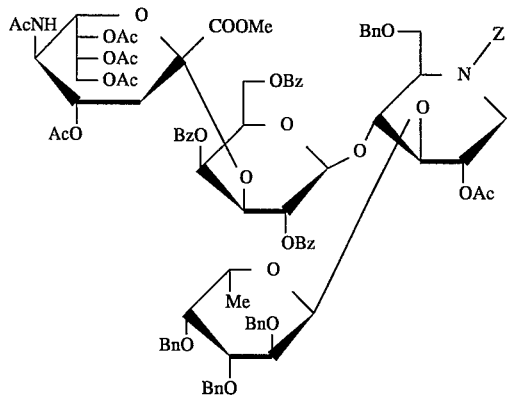

This reaction is carded out within the temperature range of 0° C.–50° C. for about 1 to 2 days. The above-mentioned basic or acidic catalysts can be used as condensing agents. It is preferable that the condensation reaction be carried out in the presence of N-iodosuccinimide (NIS) and trifluoromethanesulfonic acid. The condensation reaction may be preceded by dehydration using a desiccant if necessary.

Next, the benzyl group and the benzyloxycarbonyl group are removed by catalytic hydrogenation to yield the following compound,

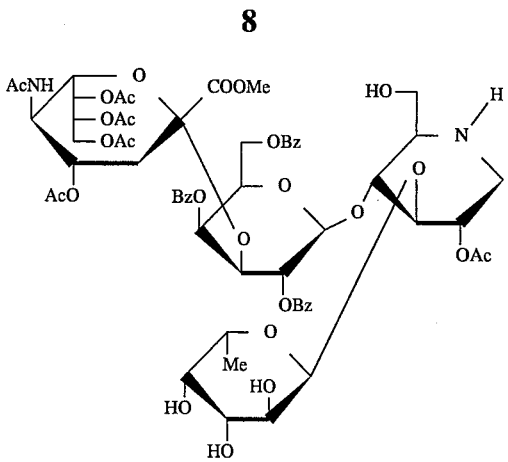

which is then reacted with an alkoxide in an alcohol solvent to remove all O-acyl (acetyl and benzoyl) groups, followed by hydrolysis of carboxylic acid methyl ester with an aqueous alkali solution and neutralization, to yield the desired compound, a sialyl Le$^x$ sugar chain containing 1-deoxynojirimycin:

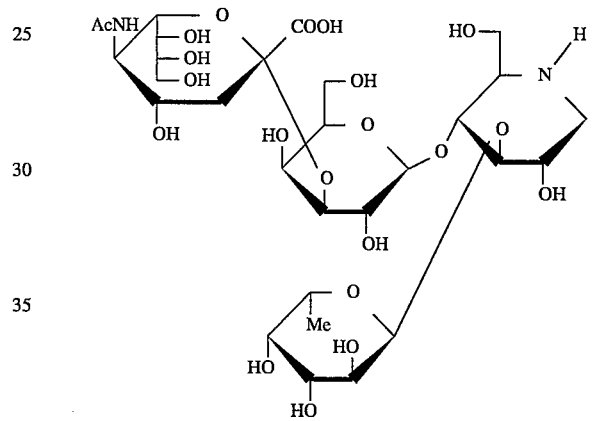

This reaction is carded out within the temperature range of 0° C.–50° C. for 1 to 2 days. Although it is preferable that the alkoxide be sodium methoxide and the alkali in aqueous solution be potassium hydroxide, these are not to be construed as limitative.

BEST MODES FOR CARRYING OUT THE INVENTION

EXAMPLES

The present invention is hereinafter illustrated in more detail by means of the following working examples and test example. Optical rotation was measured at 25° C. without exception.

[EXAMPLE 1]

Preparation of Le$^x$ and sialyl Le$^x$-type sugar chain derivatives (1) Preparation of 2,3,4,6-tetra-O-acetyl-N-tert-butoxycarbonyl-1,5-dideoxy-1,5-imino-D-glucitol:

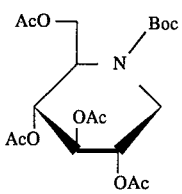

N-(tert-butoxycarbonyl)- 1,5-dideoxy- 1,5-imino-D-glucitol ( 19.36 g) was dissolved in pyridine (100 ml). To this solution, acetic anhydride (50 ml) was added, followed by overnight stirring at room temperature. After completion of the reaction, methanol (50 ml) was added at 0° C., followed by concentration under reduced pressure. The resulting residue was extracted with dichloromethane and washed with 2N hydrochloric acid and water. After drying over sodium sulfate, the extract layer was filtered and thoroughly washed with dichloromethane. The filtrate was combined with washings, followed by concentration under reduced pressure. The resulting residue was subjected to column chromatography (Wako Gel C-200, dichloromethane) to yield compound (1) (31.70 g, quantitative).

Physical property data 1. Optical rotation: $[\alpha]_D+0.71$ (C=0.842, dichloromethane) 2. Elemental analysis (for $C_{19}H_{29}NO_{10}$) Calculated.: C, 52.90%; H, 6.78%; N, 3.25% Found: C, 53.0%; H, 7.00%; N, 3.42%

(2) Preparation of 2,3,4,6-tetra-O-acetyl-N-benzyloxycarbonyl-1,5-dideoxy-1,5-imino-D-glucitol Compound (1) (21.04 g) was dissolved in dichloromethane (30 ml). To this solution, trifluoroacetic acid (18.79 ml, 5 equivalents) was added, followed by overnight stirring at room temperature. After completion of the reaction, the reaction mixture was concentrated under reduced pressure at 45° C. Ether was added to the resulting residue, followed by several decantations. The obtained solid was dissolved in methanol (30 ml). The solution was neutralized with ion exchange resin Amberlite IR-410 (OH⁻). The resin was filtered out and thoroughly washed with methanol. The filtrate was combined with washings, followed by concentration under reduced pressure. The resulting residue was dissolved in dichloromethane (40 ml) and pyridine (15 ml). To this solution, benzyl chloroformate (22.96 g, 3 equivalents) was added at 0° C., followed by overnight stirring at water temperature. After completion of the reaction, methanol was added thereto, followed by concentration under reduced pressure at 45° C. The residue was extracted with dichloromethane and washed with 2N hydrochloric acid and water. The extract layer was dried over sodium sulfate, filtered, and washed with dichloromethane. The filtrate was combined with washings, followed by concentration under reduced pressure. The resulting residue was subjected to column chromatography (Wako Gel C-200, dichloromethane) to yield compound (2) (21.53 g, 92.0%).

Physical property data 1. Optical rotation: $[\alpha]_D$- 6.06° (C=0.990, dichloromethane) 2. Elemental analysis (for $C_{22}H_{27}NO_{10}$) Calculated: C, 56.77%; H, 5.85%; N, 3.01% Found: C, 57.03%; H, 5.87%; N, 3.09%

(3) Preparation of N-benzyloxycarbonyl-1,5-dideoxy-1,5-imino-D-glucitol

Compound (2) (9.13 g) was dissolved in methanol (100 ml). To this solution, sodium methoxide was added at 0° C. until the pH became almost 12, followed by stirring at 0° C. for 1 hour. After completion of the reaction, the solution was neutralized with ion exchange resin Amberlite IR-120 (H⁺). The resin was filtered out and washed with methanol. The filtrate was combined with washings, followed by concentration under reduced pressure. The resulting residue was subjected to column chromatography (Wako Gel C-200, dichloromethane/methanol=50/1 ) to yield compound (3) (4.96 g, 85.1%).

Physical property data 1. Optical rotation: $[\alpha]_D-13.58°$ (C=0.692, methanol) 2. Elemental analysis (for $C_{14}H_{19}NO_6$) Calculated: C, 56.56%; H, 6.44%; N, 4.71% Found: C, 56.60%; H, 6.39%; N, 4.96%

(4) Preparation of 4,6-O-benzylidene-N-benzyloxycarbonyl-1,5-dideoxy-1,5-imino-D-glucitol:

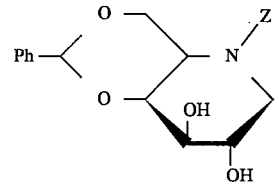

Compound (3) (9.21 g) was dissolved in N,N-dimethylformamide (27 ml). To this solution, Drierite (10 g), a desiccant, was added, followed by stirring at room temperature for 1 hour. Then, benzaldehyde dimethylacetal (13.94 ml, 3 equivalents) and a catalytic amount of p-toluenesulfonic acid were added, followed by overnight stirring at room temperature. After completion of the reaction, methanol was added thereto, and the mixture was neutralized with ion exchange resin Amberlite IR-410 (OH⁻). The resin and Drierite were filtered off, followed by washing with methanol.

The filtrate was combined with washings, followed by concentration under reduced pressure. The resulting residue was subjected to column chromatography (Wako Gel C-200, ethyl acetate/hexane=½) to yield compound (4) (8.33 g, 69.8%), which was then crystallized from ethyl acetate/hexane to yield a white crystal.

Physical property data 1. Optical rotation: $[\alpha]_D+8.69°$ (C=0.690, dichloromethane) 2. Elemental analysis (for $C_{21}H_{23}NO_6$) Calculated: C, 65.44%; H, 6.02%; N, 3.63% Found: C, 65.53%; H, 5.72%; N, 3.42%

(5) Preparation of 4,6-O-benzylidene-N-benzyloxycarbonyl-3-O-chloroacetyl-1,5-dideoxy-1,5-imino-D-glucitol Compound (4) (1 g) was dissolved in dichloromethane (80 ml). To this solution, lutidine (0.6 ml, 2 equivalents) was added. After this solution was cooled to −20° C., a solution of chloroacetyl chloride (0.25 ml, 1.2 equivalents) in dichloromethane (20 ml) was added drop by drop. The reaction mixture was stirred at −20° C. for 1.5 hours. After completion of the reaction was confirmed by TLC, the mixture was extracted with dichloromethane and washed with 2N hydrochloric acid and water. The extract layer was dried over sodium sulfate and faltered. The filtrate was combined with washings, followed by concentration under reduced pressure. The resulting residue was subjected to column chromatography (Wako Gel C-200, eluents: a) dichloromethane, b) 500:1 dichloromethane:methanol) to yield compound (5) (0.81 g, 68%) from eluate b).

Physical property data 1. Optical rotation: $[\alpha]_D-5.15°$ (C=0.582, dichloromethane) 2. Elemental analysis (for $C_{23}H_{24}NO_7Cl$) Calculated: C, 59.81%; H, 5.24%; N, 3.03% Found: C, 60.03%; H, 4.98%; N, 3.29%

(6) Preparation of 2-O-acetyl-4,6-O-benzylidene-N-benzyloxycarbonyl-3-O-chloroacetyl- 1,5odideoxy-1,5-imino-D-glucitol Compound (5) (410 mg) was dissolved in dichloromethane (4 ml) and pyridine (2 ml). After this solution was cooled to −20° C., acetyl chloride (0.1 ml, 1.5 equivalents) was added, followed by stirring at −20° C. to 0° C. for 4.5 hours. After completion of the reaction was confirmed by TLC, the reaction mixture was extracted with dichloromethane and washed with 2N hydrochloric acid and water. The extract layer was dried over sodium sulfate and filtered. The filtrate was combined with washings, followed by concentration under reduced pressure at 20° C., to yield compound (6) (450 mg, quantitative).

Physical property data 1. Optical rotation: $[\alpha]_D$ −19.48° (C=1.016, dichloromethane) 2. Elemental analysis (for $C_{25}H_{26}NO_8Cl$) Calculated: C, 59.59%; H, 5.20%; N, 2.78% Found: C, 59.69%; H, 5.14%; N, 3.05%

(7) Preparation of 2-O-acetyl-4,6-O-benzylidene-N-benzyloxycarbonyl-1,5-dideoxy- 1,5-imino-D-glucitol Compound (6) (250 mg) was dissolved in pyridine (10 ml). To this solution, water (2 ml) was added, followed by overnight stirring at room temperature. After completion of the reaction was confirmed by TLC, the reaction mixture was extracted with dichloromethane and washed with 2N hydrochloric acid and water. The extract layer was dried over sodium sulfate and filtered. The filtrate was combined with washings, followed by concentration under reduced pressure. The resulting residue was subjected to column chromatography (Wako Gel C-200, eluent: 500:1 dichloromethane:methanol) to yield compound (7) (210 mg, quantitative).

Physical property data 1. Optical rotation: $[\alpha]_D$ −12.47° (C=0.930, dichloromethane) 2. Elemental analysis (for $C_{23}H_{25}NO_7$) Calculated: C, 64.63%; H, 5.90%; N, 3.28% Found: C, 64.72%; H, 5.70%; N, 3.38%

(8) Preparation of O-(2,3,4-tri-O-benzyl-α-L-fucopyranosyl)-(1→3)-2-O-acetyl- 4,6-O-benzylidene-N-benzyloxycarbonyl-1,5-dideoxy-1,5-imino-D-glucitol:

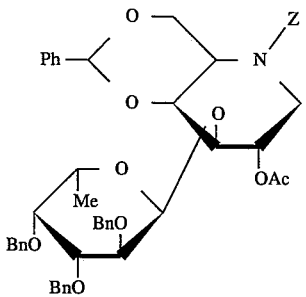

Compound (7) (30 mg) and methyl-2,3,4-tri-O-benzyl-1-thio-β-L-fucopyranoside (39 mg, 1.2 equivalents) were dissolved in benzene (16 ml). To this solution, Molecular Sieves 4A (100 mg), a desiccant, was added, followed by overnight stirring at room temperature. Next, dimethyl(methylthio)sulfonium triflate (97 mg, 4 equivalents) was added at 7° C., followed by stirring at 7° C. to room temperature for 2.5 hours. After completion of the reaction was confirmed by TLC, methanol (2 ml) and triethylamine (412) ml) were added at 0° C., followed by separation of the Molecular Sieves by filtration. Then, the filtrate was combined with washings, followed by concentration under reduced pressure. The resulting residue was extracted with dichloromethane arid washed with sodium hydrogen carbonate and water. The extract layer was dried over sodium sulfate, faltered, and concentrated under reduced pressure. The resulting residue was subjected to column chromatography (Wako Gel C-200, eluent: 1:4 ethyl acetate:hexane) to yield compound (8) (55 mg, 92%).

Physical property data 1. Optical rotation: $[\alpha]_D$ −93.64° (C=1.023, dichloromethane) 2. Elemental analysis (for $C_{50}H_{53}NO_{11}$) Calculated: C, 71.16%; H, 6.33%; N, 1.66% Found: C, 71.33%; H, 6.54%; N, 1.69%

(9) Preparation of O-(2,3,4-tri-O-benzyl-α-L-fucopyranosyl)-(1→3)-2-O-acetyl- 6-O-benzyl-N-benzyloxycarbonyl-1,5-dideoxy- 1,5-imino-D-glucitol Compound (8) (1 g) was dissolved in tetrahydrofuran (30 ml). To this solution, Molecular Sieves 3A (2 g), a desiccant, was added, followed by stirring at room temperature for 2 hours. Next, sodium cyanoborohydride (1.2 g, 15 equivalents <) was added for activation, after which hydrochloric acid/ether was added thereto drop by drop until generation of gaseous hydrogen from the reaction mixture stopped, followed by stirring at room temperature for 30 minutes. After completion of the reaction was confirmed by TLC, triethylamine was added thereto at 0° C. to neutralize the reaction mixture, followed by filtration. The Molecular Sieves was thoroughly washed with dichloromethane and methanol. The filtrate was combined with washings, followed by concentration under reduced pressure. The resulting residue was extracted with dichloromethane and washed with water. The extract layer was dried over sodium sulfate, filtered, and concentrated under reduced pressure. The resulting residue was subjected to column chromatography (Wako Gel C-200, eluent: 1:2 ethyl acetate:hexane) to yield compound (9) (810 mg, 81%).

Physical property data 1. Optical rotation: $[\alpha]_D$ −50.73° (C=0.820, dichloromethane) 2. Elemental analysis (for $C_{50}H_{55}NO_{11}$) Calculated: C, 70.99%; H, 6.55%; N, 1.66% Found: C, 71.06%; H, 6.81%; N, 1.70%

(10) Preparation of O-(2,3,4,6-tetra-O-benzoyl-β-D-galactopyranosyl)-(1→4)-O-[( 2,3,4-tri-O-benzyl-α-L-fucopyranosyl)-(1→3)]-2-O-acetyl-6-O-benzyl-N-benzyloxycarbonyl- 1,5-dideoxy-1,5-imino-D-glucitol:

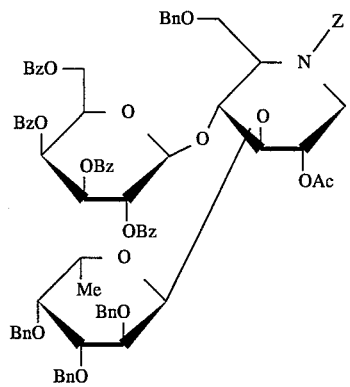

Compound (9) (130 mg)and methyl-2,3,4,6-tetra-O-benzoyl-1-thio-β-D-galactopyranoside (222 mg, 2 equivalents) were dissolved in dichloromethane (12 ml). To this solution, Molecular Sieves 4A (400 mg), a desiccant, was added, followed by overnight stirring at room temperature. After cooling the mixture to 0° C., N-iodosuccinimide (160 mg, 4 equivalents) and trifluoromethanesulfonic acid (6 μl, 0.4 equivalents) were added thereto, followed by overnight stirring at 0° C. to room temperature. After completion of the reaction was confirmed by TLC, the mixture was filtered to separate the Molecular Sieves, then extracted with dichloromethane. The extract was washed with sodium carbonate, sodium thiosulfate and water. The extract layer was dried over sodium sulfate and filtered. The filtrate was combined with washings and concentrated under reduced pressure.

The resulting residue was subjected to column chromatography (Merck Kiesel Gel 60, eluent: 1:2 ethyl acetate:hexane) to yield compound (10) (150 mg, 69%).

Physical property data 1. Optical rotation: $[\alpha]_D -10.40°$ (C=1.172, dichloromethane) 2. Elemental analysis (for $C_{84}H_{81}NO_{20}$) Calculated: C, 70.83%; H, 5.73%; N, 0.98% Found: C, 70.68%; H, 5.90%; N, 0.80%

(11) Preparation of O-(2,3,4,6-tetra-O-benzoyl-β-D-galactopyranosyl)-(1→4)-O-[(α-L-fucopyranosyl)- 1→3)]-2-O-acetyl-1,5-dideoxy-1,5-imino-D-glucitol Compound (10) (30 mg) was dissolved in methanol (3 ml) and formic acid (3 ml). To this solution, palladium black (30 mg), previously activated, was added, followed by catalytic hydrogenation at room temperature for 3 days. After completion of the reaction was confirmed by TLC, the catalyst was faltered out and washed with methanol. The filtrate was combined with washings, followed by concentration under reduced pressure. The resulting residue was subjected to column chromatography (Wako Gel C-200, eluent: 30:1 dichloromethane:methanol) to yield compound (11) (19 mg, quantitative).

Physical property data 1. Optical rotation: $[\alpha]_D -7.58°$ (C=0.343, methanol) 2. Elemental analysis (for $C_{48}H_{51}NO_{18}$) Calculated: C, 62.00%; H, 5.53%; N, 1.51% Found: C, 61.97%; H, 5.23%; N, 1.43%

(12) Preparation of O-(β-D-galactopyranosyl)-(1→4)-O-[(α-L-fucopyranosyl)-( 1→3)]-1,5-dideoxy-1,5-imino-D-glucitol Compound (11) (24 mg) was dissolved in methanol (10 ml). To this solution, sodium methoxide was added until the pH became almost 12, followed by overnight stirring at room temperature. After completion of the reaction was confirmed by TLC, the solution was neutralized with ion exchange resin Amberlite IR-120 (H+). The resin was filtered out and washed with methanol. The filtrate was combined with washings, followed by concentration under reduced pressure. The resulting residue was subjected to gel filtration (Sephadex LH-20, eluent: 3:1 ethanol:water) to yield compound (12) (16 mg, quantitative).

Physical property data 1. Optical rotation: $[\alpha]_D -23.98°$ (C=0.467, water:ethanol=2:1 ) 2. Elemental analysis (for $C_{18}H_{33}NO_{13}$) Calculated: C, 45.86%; H, 7.06%; N, 2.97% Found: C, 46.01%; H, 7.17%; N, 2.97%

(13) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→4)-O-[(2,3,4-tri-O-benzyl-α-L-fucopyranosyl)-(1→3)]-2-O-acetyl- 6-O-benzyl-N-benzyloxycarbonyl-1,5-dideoxy-1,5-imino-D-glucitol:

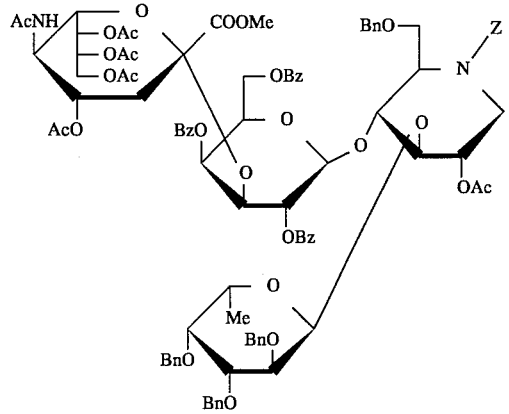

Compound (9) (70 mg) and compound B (124 mg, 1.5 equivalents) were dissolved in dichloromethane (10 ml). To this solution, Molecular Sieves 4A (250 mg), a desiccant, was added, followed by overnight stirring at room temperature. After coloring the mixture to 0° C., N-iodosuccinimide (56 mg, 3 equivalents) and trifluoromethanesulfonic acid (2.2 μl, 0.3 equivalents ) were added, followed by overnight stirring at 0° C. to room temperature. After completion of the reaction was confirmed by TLC, the Molecular Sieves was filtered out and then the filtrate was extracted with dichloromethane and washed with sodium carbonate, sodium thiosulfate and water. The extract layer was dried over sodium sulfate and filtered. The filtrate was combined with washings and concentrated under reduced pressure. The resulting residue was subjected to column chromatography (Wako Gel C-300, eluent: 3:2 ethyl acetate:hexane) to yield compound (13) (90 mg, 61%).

Physical property data 1. Optical rotation: $[\alpha]_D -10.69°$ (C=0.673, dichloromethane) 2. Elemental analysis (for $C_{97}H_{104}N_2O_{31}$) Calculated: C, 64.95%; H, 5.84%; N, 1.56% Found: C, 64.75%; H, 5.56%; N, 1.58%

(14) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galatcopyranosyl)-( 1→4)-O-[(α-L-fucopyranosyl)-(1→3)]-2-O-acetyl-1,5-dideoxy- 1,5-imino-D-glucitol Compound (13) (70 mg) was dissolved in methanol (6 ml) and acetic acid (6 ml). To this solution, palladium black (70 mg), previously activated, was added, followed by catalytic hydrogenation at room temperature for 3 days. After completion of the reaction was confirmed by TLC, the palladium was filtered out and washed with methanol. The filtrate was combined with washings, followed by concentration under reduced pressure. The resulting residue was subjected to column chromatography (Wako Gel C-200, eluent: 25:1 dichloromethane:methanol) to yield compound (14) (50 mg, quantitative).

Physical property data 1. Optical rotation: $[\alpha]_D -20.25°$ (C=0.800, methanol) 2. Elemental analysis (for $C_{61}H_{74}N_2O_{29}$) Calculated: C, 56.39%; H, 5.74%; N, 2.16% Found: C, 56.48%; H, 5.61%; N, 2.15%

(15) Preparation of O-(5-acetamido-3,5-dideoxy-D-glycero-α-D-galacto-2-nonulopyranosylonic acid)-( 2→3)-O-( [3-D-galactopyranosyl)-(1→4)-O-[(α-L-fucopyranosyl)-( 1→3)]-1,5-dideoxy-1,5-imino-D-glucitol:

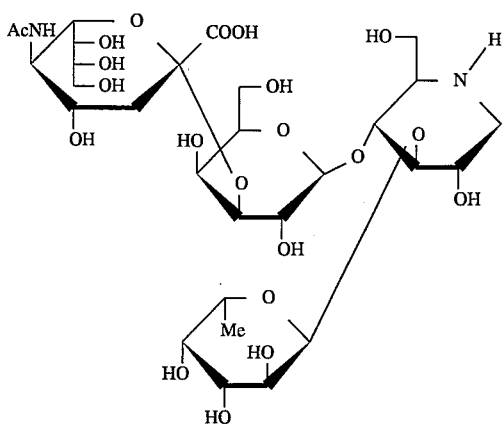

Compound (14) (50 mg) was dissolved in methanol (6 ml). To this solution, sodium methoxide was added until the pH became almost 12, followed by overnight stirring at room temperature. Then, a 0.2N aqueous solution of potassium hydroxide (2 ml) was added, followed by stirring at room temperature for 2 days. After completion of the reaction was confirmed by TLC, the mixture was neutralized with ion exchange resin Amberlite IR-120 ($H^+$). The resin was filtered out and washed with methanol and water. The filtrate was combined with washings, followed by concentration under reduced pressure. The resulting residue was subjected to gel filtration (Sephadex LH-20, eluent: 1:1 ethanol:water) to yield compound (15) (29 mg, quantitative).

Physical property data 1. Optical rotation: $[\alpha]_D -13.68°$ (C=0.833, water:ethanol=3:1) 2. Elemental analysis (for $C_{29}H_{50}N_2O_{21}$) Calculated: C, 45.67%; H, 6.61%; N, 3.67% Found: C, 45.68%; H, 6.72%; N, 3.56%

[EXAMPLE 2]

Production of Le$^a$ and sialyl Lea-type sugar chain derivatives (1) Preparation of O-(2,3,4,6-tetra-O-benzoyl-β-D-galactopyranosyl)-(1→3)-2-O-acetyl- 4,6-O-benzylidene-N-benzyloxycarbonyl-1,5-dideoxy-1,5-imino-D-glucitol 2-O-acetyl-4,6-O-benzylidene-N-benzyloxycarbonyl-1,5-dideoxy-1,5-imino-D-glucitol (1 g) and methyl-2,3,4,6-tetra-O-benzoyl-1-thio-β-D-galactopyranoside (2.9 g, 2 equivalents) were dissolved in dichloromethane (30 ml). To this solution, Molecular Sieves 4A (4 g), a desiccant, was added, followed by stirring at room temperature for 6 hours. After cooling the mixture to −20° C., N-iodosuccinimide (2.11 g, 4.0 equivalents) and trifluoromethanesulfonic acid (83 gl, 0.4 equivalents) were added, followed by overnight stirring at −20° C. to room temperature. After completion of the reaction was confirmed by TLC, the Molecular Sieves was filtered out and then the filtrate was extracted with dichloromethane and washed with sodium carbonate, sodium sulfite and water. The extract layer was added over sodium sulfate and filtered. The filtrate was combined with washings, followed by concentration under reduced pressure. The resulting residue was subjected to column chromatography (Wako Gel C-200, eluent: 1:4 ethyl acetate:hexane) to yield compound (1) (2.35 g, quantitative).

Physical property data 1. Optical rotation: $[\alpha]_D +19.85°$ (C=0.977, dichloromethane) 2. Elemental analysis (for $C_{57}H_{51}NO_{16}$) Calculated: C, 68.05%; H, 5.11%; N, 1.39% Found: C, 67.96%; H, 5.21%; N, 1.31%

(2) Preparation of O-(2,3,4,6-tetra-O-benzoyl-β-D-galactopyranosyl)-(1→3)-2-O-acetyl- 6-O-benzyl-N-benzyloxycarbonyl-1,5-dideoxy-1,5-imino-D-glucitol Compound (1) (2.35 g) was dissolved in tetrahydrofuran (50 ml). To this solution, Molecular Sieves 3A (4 g), a desiccant, was added, followed by stirring at room temperature for 2 hours. Next, sodium cyanoborohydride (2.5 g, 15 equivalents <) was added for activation, after which hydrochloric acid/ether was added drop by drop until generation of gaseous hydrogen from the reaction mixture stopped, followed by stirring at room temperature for 1 hour. After completion of the reaction was confirmed by TLC, triethylamine was added at 0° C. to neutralize the mixture. The Molecular Sieves was then filtered out and thoroughly washed with dichloromethane and methanol. The filtrate was combined with washings, followed by concentration under reduced pressure. The resulting residue was extracted with dichloromethane and washed with water. The extract layer was dried over sodium sulfate, filtered, and concentrated under reduced pressure. The resulting residue was subjected to column chromatography (Wako Gel C-200, eluent: 1:2 ethyl acetate:hexane) to yield compound (2) (2.11 g, 90%).

Physical property data 1. Optical rotation: $[\alpha]_D +62.31°$ (C=1.133, dichloromethane) 2. Elemental analysis (for $C_{57}H_{53}NO_{16}$) Calculated: C, 67.92%; H, 5.30%; N, 1.39% Found: C, 68.02%; H, 5.57%; N, 1.41%

(3) Preparation of O-(2,3,4,6-tetra-O-benzoyl-β-D-galactopyranosyl)-(1→3)-O-[( 2,3,4-tri-O-benzyl-α-L-fucopyranosyl)-(1→4)]-2-O-acetyl-6-O-benzyl-N-benzyloxycarbonyl- 1,5-dideoxy-1,5-imino-D-glucitol Compound (2) (500 mg) and methyl-2,3,4-tri-O-benzyl-1-thio-β-L-fucopyranoside (346 mg, 1.5 equivalents) were dissolved in benzene (10 ml). To this solution, Molecular Sieves 4A (1 g), a desiccant, was added, followed by overnight stirring at room temperature. After cooling the mixture to 7° C., dimethyl(methylthio)sulfonium triflate (682 mg, 4 equivalents) was added, followed by stirring at 7° C. to room temperature for 3.5 hours. After completion of the reaction was confirmed by TLC, methanol (5 ml) was added at 0° C. The mixture was neutralized with triethylamine, the Molecular Sieves was filtered out. The filtrate was combined with washings, followed by concentration under reduced pressure. The resulting residue was extracted with dichloromethane and the extract was washed with water. The extract layer was dried over sodium sulfate, filtered, and concentrated under reduced pressure. The resulting residue was subjected to column chromatography (Wako Gel C-200, eluent: 1:3 ethyl acetate:hexane) to yield compound (3) (707 mg, quantitative).

Physical property data 1. Optical rotation: $[\alpha]_D -24.50°$ (C=1.020, dichloromethane) 2. Elemental analysis (for $C_{84}H_{81}NO_{20}$) Calculated: C, 70.82%; H, 5.73%; N, 0.98% Found: C, 70.83%; H, 5.74%; N, 1.12%

(4) Preparation of O-(2,3,4,6-tetra-O-benzoyl-β-D-galactopyranosyl)-(1→3)-O-[(α-L-fucopyranosyl)-( 1→4)]-2-O-acetyl-1,5-dideoxy-1,5-imino-D-glucitol Compound (3) (100 mg) was dissolved in methanol (13 ml) and formic acid (3 ml). To this solution, palladium black (100 mg), previously catalytically hydrogenated and washed with methanol, was added, followed by catalytic hydrogenation at room temperature. After completion of the reaction was confirmed by TLC, the palladium was filtered out and washed with methanol. The filtrate was combined with washings, followed by concentration under reduced pressure. The resulting residue was subjected to column chromatography (Wako Gel C-200, eluents: a) 25:1 dichloromethane: methanol, b) 20:1 dichloromethane:methanol) to yield compound (4) (65 mg, quantitative).

Physical property data 1. Optical rotation: $[\alpha]_D$–13.02° (C=1.566, methanol) 2. Elemental analysis (for $C_{48}H_{51}NO_{18}$) Calculated: C, 62.00%; H, 5.53%; N, 1.51% Found: C, 61.93%; H, 5.74%; N, 1.77%

(5) Preparation of O-(β-D-galactopyranosyl)-(1→3)-O-[(α-L-fucopyranosyl)-(1→4)]- 1,5-dideoxy- 1,5-imino-D-glucitol Compound (4) (47 mg) was dissolved in methanol (10 ml). To this solution, sodium methoxide was added until the pH became almost 12, followed by overnight stirring at room temperature. After completion of the reaction was confirmed by TLC, the mixture was neutralized with ion exchange resin Amberlite IR-120 (H⁺). The resin was filtered out and washed with methanol and water. The filtrate was combined with washings, followed by concentration under reduced pressure. The resulting residue was subjected to gel filtration (Sephadex LH-20, eluent: 2:1 ethanol:water) to yield compound (5) (23 mg, quantitative).

Physical property data 1. Optical rotation: $[\alpha]_D$+1.01° (C=0.990, water:ethanol=2:1) 2. Elemental analysis (for $C_{18}H_{33}NO_{13}$) Calculated: C, 45.86%; H, 7.06%; N, 2.97% Found: C, 45.70%; H, 7.00%; N, 2.74%

(6) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→3)-2-O-acetyl-4,6-O-benzylidene-N-benzyloxycarbonyl-1,5-dideoxy-1,5-imino-D-glucitol 2-O-acetyl-4,6-O-benzylidene-N-benzyloxycarbonyl-1,5-dideoxy- 1,5-imino-D-glucitol (200 mg) and compound B (700 mg, 1.5 equivalents) were dissolved in dichloromethane (15 ml). To this solution, Molecular Sieves 4A (1 g), a desiccant, was added, followed by overnight stirring at room temperature. After cooling the mixture to –20° C., N-iodosuccinimide (316 mg, 3 equivalents) and trifluoromethanesulfonic acid (13 ml, 0.3 equivalents) were added, followed by overnight stirring at –20° C. to room temperature. After completion of the reaction was confirmed by TLC, the Molecular Sieves was filtered out, the filtrate was extracted with dichloromethane and washed with sodium carbonate, sodium thiosulfate and water. The extract layer was dried over sodium sulfate and filtered. The filtrate was combined with washings, followed by concentration under reduced pressure. The resulting residue was subjected to column chromatography (Merck Kiesel Gel 60, eluent: 250:4 dichloromethane:methanol) to yield compound (6) (580 mg, 90%).

Physical property data 1. Optical rotation: $[\alpha]_D$+8.81° (C=0.976, trichloromethane) 2. Elemental analysis (for $C_{70}H_{74}N_2O_{27}$) Calculated: C, 61.13%; H, 5.42%; N, 2.04% Found: C, 60.87%; H, 5.23%; N, 1.89%

(7) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→3)-2-O-acetyl-6-O-benzyl-N-benzyloxycarbonyl-1,5-dideoxy- 1,5-imino-D-glucitol Compound (6) (200 ml) was dissolved in tetrahydrofuran (30 ml). To this solution, Molecular Sieves 3A (400 mg), a desiccant, was added, followed by stirring at room temperature for 4 hours. Next, sodium cyanoborohydride (150 mg, 15 equivalents <) was added for activation, after which hydrochloric acid/ether was added drop by drop at 0° C. until generation of gaseous hydrogen from the reaction mixture stopped, followed by stirring at 0° C. for 1.5 hours. After completion of the reaction was confirmed by TLC, the mixture was neutralized with triethylamine. The Molecular Sieves was filtered out and thoroughly washed with dichloromethane and methanol. The filtrate was combined with washings, followed by concentration under reduced pressure. The resulting residue was extracted with dichloromethane. The extract layer was washed with water, followed by drying over sodium sulfate, filtered and concentrated under reduced pressure. The resulting residue was subjected to column chromatography (Merck Kiesel Gel 60, eluent: 4:1 ethyl acetate:hexane) to yield compound (7) (200 mg, quantitative).

Physical property data 1. Optical rotation: $[\alpha]_D$+26.08° (C=0.920, dichloromethane) 2. Elemental analysis (for $C_{70}H_{76}N_2O_{27}$) Calculated: C, 61.04%; H, 5.56%; N, 2.03% Found: C, 61.04%; H, 5.42%; N, 1.91%

(8) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→3)-O-[(2,3,4-tri-O-benzyl-α-L-fucopyranosyl)-(1→4)]-2-O-acetyl- 6-O-benzyl-N-benzyloxycarbonyl-1,5-dideoxy-1,5-imino-D-glucitol Compound (7) (200 mg) and compound A (101 mg, 1.5 equivalents) were dissolved in benzene (20 ml). To this solution, Molecular Sieves 4A (500 mg), a desiccant, was added, followed by overnight stirring at room temperature. After cooling the mixture to 7° C., dimethyl(methylthio)sulfonium triflate (200 mg, 4 equivalents) was added, followed by stirring at 7° C. to room temperature for 4 hours. After completion of the reaction was confirmed by TLC, methanol ( 10 ml) was added at 0° C. The mixture was neutralized with triethylamine. Then, the Molecular Sieves was filtered out. The filtrate was combined with washings, followed by concentration under reduced pressure. The resulting residue was extracted with dichloromethane. The extract layer was washed with water, and dried over sodium sulfate, filtered, and concentrated under reduced pressure. The resulting residue was subjected to column chromatography (Wako Gel C-200, eluent: 2:1 ethyl acetate:hexane) to yield compound (8) (230 mg, 89%).

Physical property data 1. Optical rotation: $[\alpha]_D$–16.49° (C=0.970, dichloromethane) 2. Elemental analysis (for $C_{97}H_{104}N_2O_{31}$) Calculated: C, 64.95%; H, 5.84%; N, 1.56% Found: C, 64.70%; H, 5.86%; N, 1.36%

(9) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→3)-O-[(α-L-fucopyranosyl)-(1→4)]-2-O-acetyl-1,5-dideoxy- 1,5-imino-D-glucitol Compound (8) (60 mg) was dissolved in methanol (10 ml) and formic acid (10 ml). To this solution, palladium black (60 mg), previously catalytically hydrogenated and washed with methanol, was added, followed by catalytic hydrogenation at room temperature. After completion of the reaction was confirmed by TLC, the palladium was filtered out and washed with methanol. The filtrate was combined with washings, followed by concentration under reduced pressure. The resulting residue was subjected to column chromatography (Wako Gel C-200, eluents: a) 25:1 dichloromethane:methanol, b) 20:1 dichloromethane:methanol) to yield compound (9) (43 mg, quantitative) from eluent b).

Physical property data 1. Optical rotation: $[\alpha]_D$–25.80° (C=1.350, methanol) 2. Elemental analysis (for $C_{61}H_{74}N_2O_{29}$) Calculated: C, 56.39%; H, 5.74%; N, 2.16% Found: C, 56.40%; H, 5.68%; N, 2.40%

(10) Preparation of O-(5-acetamido-3,5-dideoxy-D-glycero-α-D-galacto-2-nonulopyranosylonic acid)-(2→3)-O-(β-

D-galactopyranosyl)-(1→3)-O-[(α-L-fucopyranosyl)-(1→4)]-1,5-dideoxy-1,5-imino-D-glucitol Compound (9) (40 mg) was dissolved in methanol (10 ml). To this solution, sodium methoxide was added until the pH became almost 12, followed by overnight stirring at room temperature. Then, a 0.2N aqueous solution of potassium hydroxide (5 ml) was added, followed by overnight stirring at room temperature. After completion of the reaction was confirmed by TLC, the mixture was neutralized with ion exchange resin Amberlite IR-120 (H$^+$). The resin was filtered out and thoroughly washed with methanol and water. The filtrate was combined with washings, followed by concentration under reduced pressure. The resulting residue was subjected to gel filtration (Sephadex LH-20, eluent: 1:1 ethanol:water) to yield compound (10) (23 mg, quantitative).

Physical property data 1. Optical rotation: $[\alpha]_D$–4.03° (C=0.743, water:ethanol=3:1) 2. Elemental analysis (for $C_{29}H_{50}N_2O_{21}$) Calculated: C, 45.67%; H, 6.61%; N, 3.67% Found: C, 45.86%; H, 6.84%; N, 3.65%

[EXAMPLE 3]

Preparation of glucosamine-type sialyl Le$^x$ derivatives (1) Preparation of 4,6-O-benzylidene-N-benzyloxycarbonyl-3-O-chloroacetyl-1,5-dideoxy- 1,5-imino-2-O-mesyl-D-glucitol 4,6-O-benzylidene-N-benzyloxycarbonyl-3-O-chloroacetyl- 1,5-dideoxy-1,5-imino-D-glucitol (1.27 g) was dissolved in dichloromethane (50 ml) and pyridine (5 ml). To this solution, methanesulfonyl chloride (0.38 ml, 1.8 equivalents) was added at –20° C., followed by stirring at –20° C. to 0° C. for 8 hours. After completion of the reaction was confirmed by TLC, the mixture was extracted with dichloromethane and washed with 2N hydrochloric acid and water. The extract layer was dried over sodium sulfate and filtered. The filtrate was combined with washings, followed by concentration under reduced pressure to yield compound (1) (1.49 g, quantitative).

Physical property dam 1. Optical rotation: $[\alpha]_D$–16.28° (C=1.253, trichloromethane) 2. Elemental analysis (for $C_{24}H_{26}N_2O_9SCl$) Calculated: C, 53.38%; H, 4.85%; N, 2.59% Found: C, 53.40%; H, 4.62%; N, 2.87%

(2) Preparation of 2,3-anhydro-4,6-O-benzylidene-N-benzyloxycarbonyl-1,5-dideoxy- 1,5-imino-D-mannitol Compound (1) (1.4 g) was dissolved in 1,4-dioxane (5 ml) and methanol (15 ml). After cooling the solution to 0° C., sodium methoxide (0.89 ml, 6 equivalents) was added, followed by stirring at 0° C. for 5 minutes. After completion of the reaction was confirmed by TLC, the mixture was concentrated under reduced pressure at 20° C. The resulting residue was extracted with dichloromethane. The extract layer was washed with water followed by drying over sodium sulfate and filtered. The filtrate was combined with washings, followed by concentration under reduced pressure at 20° C. The resulting residue was subjected to column chromatography (Wako Gel C-200, eluent: 400:1 dichloromethane:methanol) to yield compound (2) (0.95 g, quantitative).

Physical property data 1. Optical rotation: $[\alpha]_D$+46.65° (C=0.853, dichloromethane) 2. Elemental analysis (for $C_{21}H_{21}NO_5$) Calculated: C, 68.65%; H, 5.76%; N, 3.81% Found: C, 68.64%; H, 5.90%; N, 3.61%

(3) Preparation of 2-azide-4,6-O-benzylidene-N-benzyloxycarbonyl- 1,2,5-trideoxy- 1,5-imino-D-glucitol Compound (2) (3.71 g) was dissolved in N,N-dimethylformamide (15 ml). To this solution, sodium azide (6.56 g, 10 equivalents ) was added, followed by overnight stirring at 110° C. After completion of the reaction was confirmed by TLC, the sodium azide was filtered out, followed by concentration under reduced pressure. The resulting residue was extracted with dichloromethane. The extract layer was washed with water, dried over sodium sulfate and filtered. The filtrate was combined with washings, followed by concentration under reduced pressure. The resulting residue was subjected to column chromatography (Wako Gel C-200, eluent: 1:3 ethyl acetate:hexane) to yield compound (3) (1.66 g, 40%).

Physical property data 1. Optical rotation: $[\alpha]_D$–15.95° (C=1.216, dichloromethane) 2. Elemental analysis (for $C_{21}H_{22}N_4O_5$) Calculated: C, 61.46%; H, 5.40%; N, 13.65% Found: C, 61.56%; H, 5.29%; N, 13.70%

(4) Preparation of 2-acetamido-4,6-O-benzylidene-N-benzyloxycarbonyl-1,2,5-trideoxy- 1,5-imino-D-glucitol Compound (3) (280 mg) was dissolved in 1,2-dichloromethane (10 ml). After heating the solution to 45° C., triphenylphosphine (385 mg, 2 equivalents) was added, followed by stirring at 45° C. for 30 minutes. Next, water (0.15 ml, 10 equivalents <) was added, followed by overnight stirring at 45° C. After completion of the reaction was confirmed by TIE, the mixture was concentrated under reduced pressure. The resulting residue was dissolved in methanol (10 ml). To this solution, acetic anhydride (71 μl, 1.1 equivalents) was added, followed by stirring at room temperature for 4 hours. After completion of the reaction was confirmed, pyridine (2 ml) was added at 0° C., followed by concentration under reduced pressure. The resulting residue was extracted with dichloromethane and washed with 2N hydrochloric acid and water. The extract layer was dried over sodium sulfate and filtered. The filtrate was combined with washings, followed by concentration under reduced pressure. The resulting residue was subjected to column chromatography (Wako Gel C-200, eluents: a) 80:1 dichloromethane:methanol, b) 50:1 dichloromethane:methanol) to yield compound (4) (270 mg, 93%) from eluent b).

Physical property data 1. Optical rotation: $[\alpha]_D$+3.22° (C=0.743, dichloromethane) 2. Elemental analysis (for $C_{23}H_{26}N_2O_6$) Calculated: C, 64.78%; H, 6.15%; N, 6.57% Found: C, 64.51%; H, 6.36%; N, 6.39%

(5) Preparation of O-(2,3,4-tri-O-benzyl-α-L-fucopyranosyl)-(1→3)-2-acetamido- 4,6-O-benzylidene-N-benzyloxycarbonyl-1,2,5-trideoxy-1,5-imino-D-glucitol Compound (4) (250 mg) and methyl-2,3,4-tri-O-benzyl-1-thio-β-L-fucopyranoside (compound A) (372 mg, 1.2 equivalents) were dissolved in benzene (20 ml). To this solution, Molecular Sieves 4A (700 mg), a desiccant, was added, followed by overnight stirring at room temperature. Next, dimethyl(methylthio)sulfonium triflate (608 mg, 4.0 equivalents) was added thereto at 7° C., followed by stirring at 7° C. to room temperature for 3 hours. After completion of the reaction was confirmed by TLC, methanol (10 ml) was added at 0° C. The mixture was neutralized with triethylamine and filtered to separate the Molecular Sieves. The filtrate was then combined with washings, followed by concentration under reduced pressure. The resulting residue was extracted with dichloromethane. The extract layer washed with water, dried over sodium sulfate and filtered, followed by concentration under reduced pressure. The resulting residue was subjected to column chromatography (Wako Gel C-200, eluent: 1:2 ethyl acetate:hexane) to yield compound (5) (494 mg, quantitative).

Physical property data 1. Optical rotation: $[\alpha]_D$–83.24° (C=0.973, dichloromethane) 2. Elemental analysis (for $C_{50}H_{54}N_2O_{10}$) Calculated: C, 71.24%; H, 6.46%; N, 3.32% Found: C, 71.31%; H, 6.36%; N, 3.61%

(6) Preparation of O-(2,3,4-tri-O-benzyl-α-fucopyranosyl)-(1→3)-2-acetamido- 6-O-benzyl-N-benzyloxycarbonyl-1,2,5-trideoxy-1,5-imino-D-glucitol Compound (5) (494 mg) was dissolved in tetrahydrofuran (30 ml). To this solution, Molecular Sieves 3A (1 g), a desiccant, was added, followed by stirring at room temperature for 3 hours. Next, sodium cyanoborohydride (600 mg, 15 equivalents <) was added for activation, after which hydrochloric acid/ether was added drop by drop until generation of gaseous hydrogen from the reaction mixture stopped, followed by stirring at room temperature for 4 hours. After completion of the reaction was confirmed by TLC, triethylamine was added at 0° C. to neutralize the mixture. The Molecular Sieves was filtered out and thoroughly washed with dichloromethane and methanol. The filtrate was combined with washings, followed by concentration under reduced pressure. The resulting residue was extracted with dichloromethane. The extract layer was washed with water, dried over sodium sulfate and filtered. The filtrate was concentrated under reduced pressure, and the resulting residue was subjected to column chromatography (Wako Gel C-200, eluent: 1:1 ethyl acetate:hexane) to yield compound (6) (495 mg, quantitative).

Physical property dam 1. Optical rotation: $[\alpha]_D$–15.39° (C=0.926, dichloromethane) 2. Elemental analysis (for $C_{50}H_{56}N_2O_{10}$) Calculated: C, 71.07%; H, 6.68%; N, 3.32% Found: C, 71.28%; H, 6.81%; N, 3.28%

(7) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→4)-O-[(2,3,4-tri-O-benzyl-α-L-fucopyranosyl)-(1→3)]-2-acetamido- 6-O-benzyl-N-benzyloxycarbonyl-1,2,5-trideoxy-1,5-imino-D-glucitol Compound (6) (130 mg) and compound B (230 mg, 1.5 equivalents) were dissolved in dichloromethane (20 ml). To this solution, Molecular Sieves 4A (400 mg), a desiccant, was added, followed by overnight stirring at room temperature. After cooling the mixture to −20° C., N-iodosuccinimide (110 mg, 3 equivalents) and trifluoromethanesulfonic acid (5 μl, 0.3 equivalents) were added, followed by overnight stirring at −20° C. to room temperature. After completion of the reaction was confirmed by TLC, the Molecular Sieves was filtered out. The reaction mixture was extracted with dichloromethane. The extract layer was washed with sodium carbonate, sodium sulfite and water, followed by drying over sodium surf ate and filtered. The filtrate was combined with washings, followed by concentration under reduced pressure. The resulting residue was subjected to column chromatography (Merck Kiesel Gel 60, eluent: 2:1 ethyl acetate:hexane) to yield compound (7) (111 mg, 40%).

Physical property data 1. Optical rotation: $[\alpha]_D$–6.91° (C=1.214, dichloromethane) 2. Elemental analysis (for $C_{97}H_{105}N_3O_{30}$) Calculated: C, 64.98%; H, 5.90%; N, 2.34% Found: C, 65.11%; H, 6.18%; N, 2.35%

(8) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→4)-O-[(α-L-fucopyranosyl)-(1→3)]-2-acetamido-1,2,5-trideoxy-N-methyl- 1,5-imino-D-glucitol Compound (7) (66 mg) was dissolved in methanol (10 ml) and formic acid (10 ml). To this solution, palladium black (66 mg), previously catalytically hydrogenated and washed with methanol, was added, followed by catalytic hydrogenation at room temperature for 10 days. After completion of the reaction was confirmed by TLC, the palladium was filtered out and washed with methanol. The filtrate was combined with washings, followed by concentration under reduced pressure. The resulting residue was subjected to column chromatography (Wako Gel C-200, eluent: 15:1 dichloromethane:methanol) to yield compound (8) (48 mg, quantitative).

Physical property data 1. Optical rotation: $[\alpha]_D$–19.20° (C=1.583, methanol) 2. Elemental analysis (for $C_{62}H_{77}N_3O_{28}$) Calculated: C, 56.75%; H, 5.91%; N, 3.20% Found: C, 56.61%; H, 6.08%; N, 3.02%

(9) Preparation of O-(5-acetamido-3,5-dideoxy-D-glycero-α-D-galacto-2-nonulopyranosylonic acid)-(2→3)-O-(β-D-galactopyranosyl)-(1→4)-O-[(α-L-fucopyranosyl)-( 1→3)]-2-acetamido-1,2,5-trideoxy-N-methyl-1,5-imino-D-glucitol Compound (8) (44 mg) was dissolved in methanol (10 ml). To this solution, sodium methoxide was added until the pH became almost 12, followed by overnight stirring at room temperature. Then, a 0.2N aqueous solution of potassium hydroxide (5 ml) was added, followed by overnight stirring at room temperature. After completion of the reaction was confirmed by TLC, the solution was neutralized with ion exchange resin Amberlite IR-120 ($H^+$). The resin was filtered out and thoroughly washed with methanol and water. The filtrate was combined with washings, followed by concentration under reduced pressure. The resulting residue was subjected to gel filtration (Sephadex LH-20, eluent: 1:3 ethanol:water) to yield compound (9) (29 mg, quantitative).

Physical property data 1. Optical rotation: $[\alpha]_D$–3.93° (C=0.966, water:ethanol=4:1) 2. Elemental analysis (for $C_{32}H_{55}N_3O_{21}$) Calculated: C, 47.00%; H, 6.78%; N, 5.14% Found: C, 46.97%; H, 6.48%; N, 5.06%

(10) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-( 1→3)-2-acetamido-4,6-O-benzylidene-N-benzyloxycarbonyl- 1,2,5-trideoxy-1,5-imino-D-glucitol Compound (4) (150 mg) and compound B (525 mg, 1.5 equivalents) were dissolved in dichloromethane (15 ml). To this solution, Molecular Sieves 4A (800 mg), a desiccant, was added, followed by stirring at room temperature for 5 hours. After cooling the mixture to −20° C., N-iodosuccinimide (237 mg, 3 equivalents) and trifluoromethanesulfonic acid (10 μl, 0.3 equivalents) were added, followed by overnight stirring at −20° C. to room temperature. After completion of the reaction was confirmed by TLC, the Molecular Sieves was filtered out. The filtrate was extracted with dichloromethane and washed with sodium carbonate, sodium sulfite and water. The extract layer was dried over sodium surf ate and faltered. The filtrate was combined with washings, followed by concentration under reduced pressure. The resulting residue was subjected to column chromatography (Merck Kiesel Gel 60, eluents: a) 3:1 ethyl acetate:hexane, b) 4:1 ethyl acetate:hexane) to yield compound (10) (220 mg, 46%).

Physical property data 1. Optical rotation: $[\alpha]_D$–0.24° (C=0.816, dichloromethane) 2. Elemental analysis (for $C_{70}H_{75}N_3O_{26}$) Calculated: C, 61.18%; H, 5.50%; N, 3.06% Found: C, 61.11%; H, 5.69%; N, 3.21%

(11) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-(1→3)-2-acetamido-6-O-benzyl-N-benzyloxycarbonyl-1,2,5-trideoxy- 1,5-imino-D-glucitol Compound (10) (190 mg) was dissolved in tetrahydrofuran (30 ml). To this solution, Molecular Sieves 3A (400 mg), a desiccant, was added, followed by stirring at room temperature for 5 hours. Next, sodium cyanoborohydride (170 mg, 15 equivalents <) was added for activation, followed by stirring at 0° C. for 4.5 hours. After completion of the reaction was confirmed by TLC, the mixture was neutralized with triethylamine. The Molecular Sieves was filtered out and thoroughly washed with dichloromethane and methanol. The filtrate was combined with washings, followed by concentration under reduced pressure. The resulting residue was extracted with dichloromethane. The extract layer was washed with water, and dried over sodium sulfate and filtered. The tiltrate was concentrated under reduced pressure. The resulting residue was subjected to column chromatography (Wako Gel C-200, eluent: 4:1 ethyl acetate:hexane) to yield compound (11) (190 mg, quantitative).

Physical property data 1. Optical rotation: $[\alpha]_D$+16.04° (C=0.723, dichloromethane) 2. Elemental analysis (for $C_{70}H_{77}N_3O_{26}$) Calculated: C, 61.09%; H, 5.64%; N, 3.05% Found: C, 60.82%; H, 5.55%; N, 3.11%

(12) Preparation of O-(methyl 5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-(1→3)-O-[(2,3,4-tri-O-benzyl-α-L-fucopyranosyl)-(1→4)]-2-acetamido- 6-O-benzyl-N-benzyloxycarbonyl-1,2,5-trideoxy-1,5-imino-D-glucitol Compound (11) (70 mg) and compound A (35 mg, 1.5 equivalents) were dissolved in benzene (15 ml). To this solution, Molecular Sieves 4A (200 mg), a desiccant, was added, followed by stirring overnight at room temperature. After cooling the mixture to 7° C., N-iodosuccinimide (35 mg, 3 equivalents) and trifluoromethanesulfonic acid (1.5 μl, 0.3 equivalents) were added thereto, followed by stirring at 7° C. to room temperature for 5 hours. After completion of the reaction was confirmed by TLC, the Molecular Sieves was filtered out. The filtrate was extracted with dichloromethane and the extract was washed with sodium carbonate, sodium sulfite and water. The extract layer was dried over sodium sulfate and filtered. The filtrate was combined with washings, followed by concentration under reduced pressure. The resulting residue was subjected to column chromatography (Wako Gel C-200, eluent: 3:1 ethyl acetate:hexane) to yield compound (12) (50 mg, 55%).

Physical property data 1. Optical rotation: $[\alpha]_D$–18.74° (C=1.462, dichloromethane) 2. Elemental analysis (for $C_{97}H_{105}N_3O_{30}$) Calculated: C, 64.98%; H, 5.90%; N, 2.34% Found: C, 65.13%; H, 6.01%; N, 2.62%

(13) Preparation of O-(methyl-5-acetamido-4,7,8,9-tetra-O-acetyl-3,5-dideoxy-D-glycero-α-D-galacto- 2-nonulopyranosylonate)-(2→3)-O-(2,4,6-tri-O-benzoyl-β-D-galactopyranosyl)-(1→3)-O-[(α-L-fucopyranosyl)-(1→4)]-2-acetamido-1,2,5-trideoxy-N-methyl- 1,5-imino-D-glucitol Compound (12) (61 mg) was dissolved in methanol (10 ml) and formic acid (10 ml). To this solution, palladium black (60 mg), previously catalytically hydrogenated and washed with methanol, was added, followed by catalytic hydrogenation at room temperature while stirring for 7 days. After completion of the reaction was confirmed by TLC, the palladium was filtered out and washed with methanol. The filtrate was combined with washings, followed by concentration under reduced pressure. The resulting residue was subjected to column chromatography (Wmko Gel C-200, eluents: a) acetone, b) methanol) to yield compound (13) (44 mg, quantitative).

Physical property data 1. Optical rotation: $[\alpha]_D$–9.18° (C=1.481, methanol) 2. Elemental analysis (for $C_{62}H_{77}N_3O_{28}$) Calculated: C, 56.75%; H, 5.91%; N, 3.20% Found: C, 56.50%; H, 5.87%; N, 3.49%

(14) Preparation of O-(5-acetamido-3,5-dideoxy-D-glycero-α-D-galacto-2-nonulopyranosylonic acid)-(2→3)-O-(β-D-galactopyranosyl)-(1→3)-O-[(α-L-fucopyranosyl)-(1→4)]-2-acetamido- 1,2,5-trideoxy-N-methyl-1,5-imino-D-glucitol Compound (13) (30 mg) was dissolved in methanol (10 ml). To this solution, sodium methoxide was added until the pH became almost 12, followed by overnight stirring at room temperature. Then, a 0.2N aqueous solution of potassium hydroxide (6 ml) was added, followed by stirring at room temperature for 2 days. After completion of the reaction was confirmed by TLC, the mixture was neutralized with ion exchange resin Amberlite IR-120 ($H^+$). The resin was filtered out and thoroughly washed with methanol and water. The tiltrate was combined with washings, followed by concentration under reduced pressure. The resulting residue was subjected to gel filtration (Sephadex LH-20, eluent: 1:3 ethanol:water) to yield compound (14) (19 mg, quantitative).

Physical property data 1. Optical rotation: $[\alpha]_D$–23.47° (C=0.230, water:ethanol=4:1) 2. Elemental analysis (for $C_{32}H_{55}N_3O_{21}$) Calculated: C, 47.00%; H, 6.78%; N, 5.14% Found: C, 46.80%; H, 6.50%; N, 5.16%

[EXAMPLE 4]

Preparation of N-methyl $Le^a$-type sugar chain derivatives

The same procedure as above was followed to yield O-(β-D-galactopyranosyl)-(1→3)-O-[(α-L-fucopyranosyl)-(1→4)]-1,5-dideoxy-N-methyl-1,5-imino-D-glucitol.

Physical property data 1. Optical rotation: $[\alpha]_D$+1° (C=0.500, water:ethanol=2:1) 2. Elemental analysis (for $C_{19}H_{35}NO_{13}$) Calculated: C, 47.01%; H, 7.27%; N, 2.89% Found: C, 47.02%; H, 7.38%; N, 2.78%

[EXAMPLE 5]

Preparation of N-methyl $SLe^a$-type sugar chain derivative

The same procedure as above was followed to yield O-(5-acetamido-3,5-dideoxy-D-glycero-α-D-galacto-2-nonulopyranosylonic acid)-(2→3)-O-(β-D-galactopyranosyl)-(1→3)-O-[(α-L-fucopyranosyl)-(1→4)]-1,5-dideoxy-N-methyl-1,5-imino-D-glucitol.

Physical property data 1. Optical rotation: $[\alpha]_D -26°$ (C=0.500, water:ethanol=4:1) 2. Elemental analysis (for $C_{30}H_{52}N_2O_{21}$) Calculated: C, 46.39%; H, 6.75%; N, 3.61% Found: C, 46.29%; H, 6.91%; N, 3.62%

The present invention is hereinafter described in more detail by means of the following test example.

[TEST EXAMPLE]

Effects of synthetic sugar chains on binding of activated human vascular endothelial cells and cultured human leukemia cell HL60

Cell culture

Cultured human vascular endothelial cells were isolated from the umbilical vein via collagenase treatment and cultured in a flask for culture, coated with 1% gelatin or at the concentration of 0.02 mg/cm² fibronectin. The growth medium used was prepared by adding 15% fetal calf serum (FCS), 45 mg/lECGS, 90 mg/l heparin and 40 mg/l gentamycin to 199 medium. Cultured human leukemia cell HL60 was grown and maintained in RPMI1640 medium containing 10% FCS. For both types of cells, culture was conducted in a $CO_2$ incubator (5% $CO_2$, 95% air) at 37° C.

Measurement of cell adhesion

Cultured human umbilical venous cells (HUVEC) were seeded over a 96-well culture plate coated with 0.1% gelatin, and cultured on growth medium until they became confluent. The cells were washed with Dulbecco's modified Eagle medium (DMEM) containing 10% FCS, and cultured for 4 hours in a 37° C. $CO_2$ incubator after adding 100 µl of 10% FCS DMEM containing recombinant human interleukin-1β (IL-1β) (activation). The HL60 cells were twice washed with serum-free DMEM, suspended in Hanks' solution containing 0.5% glutaraldehyde, and fixed, with ice cooling, for 30 minutes. After fixation, the cells were twice washed with serum-free DMEM to remove the fixative. Then, the number of cells was adjusted to 2×10⁶ cells/ml using DMEM containing 10% FCS, and stored in ice until using. After activation, the HUVEC was washed with DMEM containing 10% FCS, and incubated at room temperature for 30 minutes after adding 50 µl of 10% FCS DMEM containing either an anti-ELAM-1 antibody (BBA 2, British Biotechnology Lid, Abinton) or a sample. The fixed HL60 cells were added at 50 µl per well, followed by incubation at room temperature for 45 minutes. After unbound cells were washed out, the central portion of each well was photographed. The adhesive cells seen in the imaging field were counted. The effect obtained by the addition of the sample was assessed as a percent ratio to the number of HL60 cells bound to the IL-1β-activated HUVEC. The results are given in Tables 1 and 2.

Table 1 shows that the $SLe^x$ derivative of the compound (15) of the invention, described in Example 1, and the $Le^x$ derivative of compound (12), described in Example 1, suppressed the HL60 cell adhesion to the IL-1β-activated HUVEC by 29.9% and 37.6%, respectively, when they were present at a concentration of 100 µg/ml, demonstrating ELAM-1-dependent cell adhesion inhibitory activity.

Table 2 shows that the $SLe^x$ derivative of the compound (9) of the invention, described in Example 3, the $SLe^a$ derivative of compound (14), described in Example 3, the $Le^a$ derivative described in Example 4, and the $SLe^a$ derivative described in Example 5, suppressed the HL60 cell adhesion to IL-1β-activated HUVEC by 49.6%, 43.1%, 29.8% and 71.1%, respectively, when they were present at a concentration of 100 µg/ml, demonstrating ELAM-1-dependent cell adhesion inhibitory activity.

TABLE 1

Inhibitory action of $SLe^x$ and $Le^x$-type sugar chain derivatives on ELAM-1-dependent adhesion of cultured human leukemia cell HL60

| Treatment | contentration (µg/ml) | Number of samples | Number of adhering cells (%) | |
|---|---|---|---|---|
| Basal | | 5 | 36.8 | (28.1) |
| Control | | 5 | 131.0 | (100.0) |
| α-ELAM | 50 | 5 | 27.6 | (21.1) |
| Example 1 (15) | 10 | 5 | 117.8 | (89.9) |
| Example 1 (15) | 100 | 5 | 91.8 | (70.1) |
| Example 1 (12) | 10 | 5 | 120.0 | (91.6) |
| Example 1 (12) | 100 | 5 | 81.8 | (62.4) |

Note:
"Basal" shows adhesion to non-activated HUVEC;
"Control" shows adhesion to HUVEC activated with 10 U/ml IL-1β;
"α-ELAM" shows adhesion to activated HUVEC in the case which anti-ELAM-1 antibody was added;
"Example 1 (15)" shows adhesion to activated HUVEC in the case which an $SLe^x$-type substance, inventive compound (15) described in Example 1 was added;
"Example 1 (12)" shows adhesion to activated HUVEC in the case which an $Le^x$-type substance, compound (12) described in Example 1 was added.

TABLE 2

Inhibitory action of $SLe^a$, $Le^a$ and $SLe^x$-type sugar chain derivatives on ELAM-1-dependent adhesion of cultured human leukemia cell HL60

| Treatment | contentration (µg/ml) | Number of samples | Number of adhering cells (%) | |
|---|---|---|---|---|
| Basal | | 5 | 28.2 | (7.4) |
| Control | | 5 | 383.4 | (100.0) |
| α-ELAM | 25 | 5 | 75.0 | (19.6) |
| Example 3 (9) | 100 | 5 | 193.2 | (50.4) |
| Example 3 (14) | 100 | 5 | 218.2 | (56.9) |
| Example 4 | 100 | 5 | 269.0 | (70.2) |
| Example 5 | 100 | 5 | 110.8 | (28.9) |

Note:
"Basal" shows adhesion to non-activated HUVEC;
"Control" shows adhesion to HUVEC activated with 10 U/ml IL-1β;
"α-ELAM" shows adhesion to activated HUVEC in the case which anti-ELAM-1 antibody was added;
"Example 3 (9)" shows adhesion to activated HUVEC in the case that an $SLe^x$-type substance, inventive compound (9) described in Example 3 was added;
"Example 3 (14)" shows adhesion to activated HUVEC in the case which an $SLe^a$-type substance of compound (14) described in Example 3 was added;
"Example 4" shows adhesion to activated HUVEC in the case that an $Le^a$-type substance, the compound described in Example 4 was added;
"Example 5" shows adhesion to activated HUVEC in the case that an $SLe^a$-type substance, the compound described in Example 5 was added.

When administered as a pharmaceutical, the compounds of the present invention can be administered as such or in a pharmaceutical composition comprising 0.1 to 99.5%, preferably 0.5 to 90% of the compound in a pharmaceutically acceptable nontoxic inert carrier, to animals, including humans.

At least one solid, semi-solid or liquid diluents, filling agents, and other formulation aids are used as carriers. It is desirable that the pharmaceutical composition be administered in an administration unit form. The pharmaceutical composition according to the present invention can be administered orally, intratissularly, topically (percutaneous administration etc.) or perfectally, in dosage forms suitable thereto. For example, intratissular administration is preferred.

It is desirable that the dose of the compound of the present invention, as an anti-inflammatory agent, be chosen in view of age, body weight and other factors of the patient, route of administration, nature and severity of the target disease and other factors. The dose range is usually from 100 mg to 3 g/day, preferably from 500 mg to 1 g/day for each adult, as the amount of the active ingredient of the present invention. As the case may be, the dose may be lower or higher. It is also desirable that the daily dose be divided in one to three portions.

What is claimed is:

1. A Lewis-type sugar chain derivative represented by the following formula: wherein $R^1$ represents hydrogen, a lower alkyl, a lower alkenyl or a lower alkynyl; $R^2$ and $R^3$ differ from each other and represent a galactosyl, sialylgalactosyl or fucosyl group; and $R^4$ represents a hydroxyl group or an acetamido group:

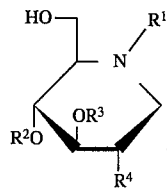

2. A Lewis X derivative, according to claim 1, represented by the following formula:

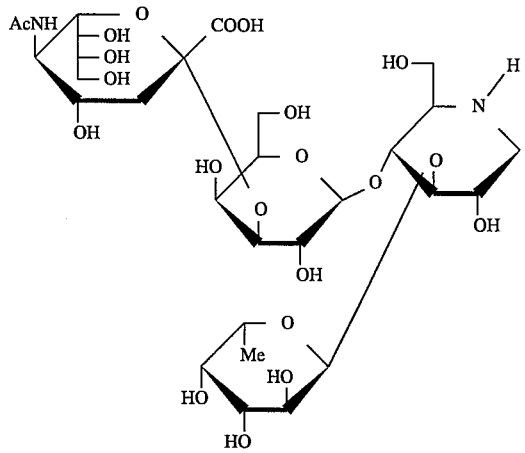

3. A Lewis X derivative, according to claim 1, represented by the following formula:

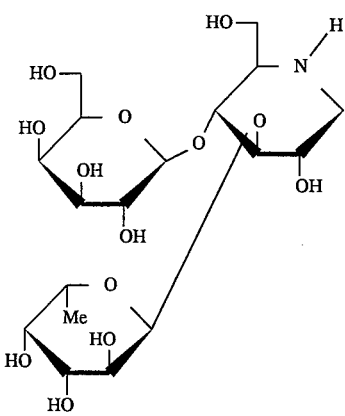

4. A Lewis X derivative, according to claim 1, represented by the following formula:

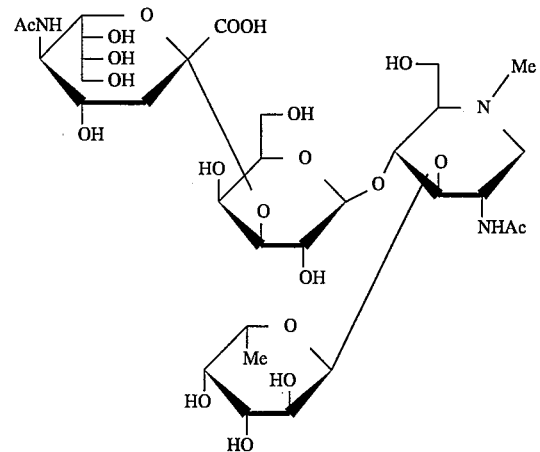

5. A Lewis A derivative, according to claim 1, represented by the following formula:

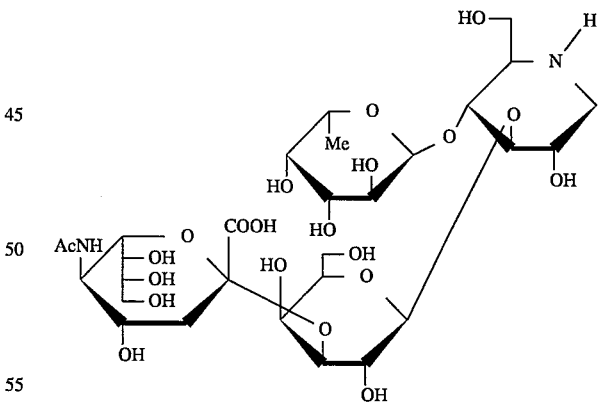

6. A Lewis A derivative, according to claim 1, represented by the following formula:

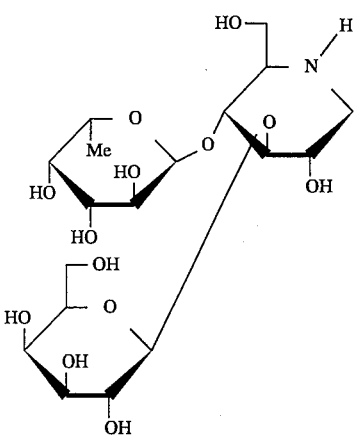

7. A Lewis A derivative, according to claim 1, represented by the following formula:

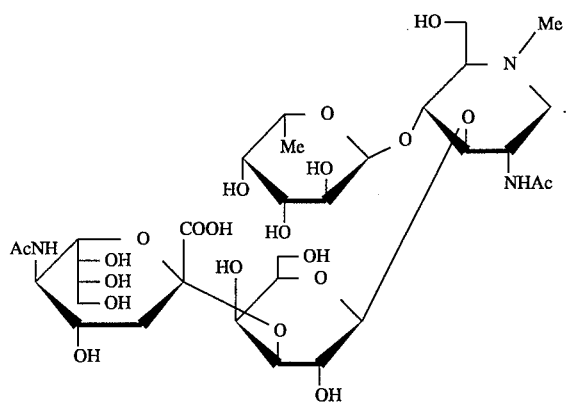

8. A Lewis A derivative, according to claim 1, represented by the following formula:

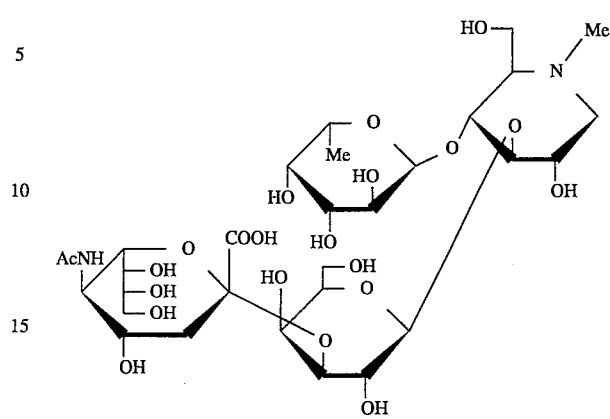

9. A method for inhibiting cell adhesion in mammals, which comprises administering to a mammal in need thereof an effective amount of the compound of claim 1, or a pharmaceutically acceptable salt thereof or a solvate of said compound or said salt in combination with a pharmaceutically acceptable carrier.

10. A pharmaceutical composition useful for inhibiting cell adhesion in mammals, which comprises a therapeutically effective amount of the compound of claim 1, or a pharmaceutically acceptable salt thereof or a solvate of said compound or said salt in combination with a pharmaceutically acceptable carrier.

* * * * *